(12) United States Patent
Ollerdessen et al.

(10) Patent No.: US 7,869,849 B2
(45) Date of Patent: Jan. 11, 2011

(54) OPAQUE, ELECTRICALLY NONCONDUCTIVE REGION ON A MEDICAL SENSOR

(75) Inventors: Albert L. Ollerdessen, Danville, CA (US); Bradford B. Chew, San Ramon, CA (US); Phillip S. Palmer, San Leandro, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 605 days.

(21) Appl. No.: 11/527,762

(22) Filed: Sep. 26, 2006

(65) Prior Publication Data

US 2008/0076982 A1    Mar. 27, 2008

(51) Int. Cl.
*A61B 5/1455* (2006.01)
(52) U.S. Cl. ...................... 600/323; 600/344
(58) Field of Classification Search ................ 600/310, 600/323, 344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |

(Continued)

FOREIGN PATENT DOCUMENTS

DE            3405444            8/1985

(Continued)

OTHER PUBLICATIONS

U.S. Appl. No. 11/507,814, filed Aug. 22, 2006, Baker et al.

(Continued)

*Primary Examiner*—Eric F Winakur
(74) *Attorney, Agent, or Firm*—Fletcher Yoder

(57) ABSTRACT

A medical sensor may be adapted to prevent unwanted light and electrical interference from corrupting physiological measurements. Sensors are provided with features that reduce the amount of outside light or shunted light that impinge the detecting elements of the sensor. The sensor is adapted to reduce crosstalk between electrical signals, increasing the accuracy of measurements. The sensor is also adapted to reduce the effect of outside light or shunted light on pulse oximetry measurements.

31 Claims, 5 Drawing Sheets

U.S. PATENT DOCUMENTS

| | | | |
|---|---|---|---|
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE033,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |

| | | | | | |
|---|---|---|---|---|---|
| 5,349,952 A | 9/1994 | McCarthy et al. | 5,577,500 A | 11/1996 | Potratz |
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,991 A | 4/1997 | Sloane |
| 5,372,136 A | 12/1994 | Steuer et al. | 5,619,992 A | 4/1997 | Guthrie et al. |
| 5,377,675 A | 1/1995 | Ruskewicz et al. | 5,626,140 A | 5/1997 | Feldman et al. |
| 5,385,143 A | 1/1995 | Aoyagi | 5,630,413 A | 5/1997 | Thomas et al. |
| 5,387,122 A | 2/1995 | Goldberger et al. | 5,632,272 A | 5/1997 | Diab et al. |
| 5,390,670 A | 2/1995 | Centa et al. | 5,632,273 A | 5/1997 | Suzuki |
| 5,392,777 A | 2/1995 | Swedlow et al. | 5,634,459 A | 6/1997 | Gardosi |
| 5,398,680 A | 3/1995 | Polson et al. | 5,638,593 A | 6/1997 | Gerhardt et al. |
| 5,402,777 A | 4/1995 | Warring et al. | 5,638,816 A | 6/1997 | Kiani-Azarbayjany et al. |
| 5,402,779 A | 4/1995 | Chen et al. | 5,638,818 A | 6/1997 | Diab et al. |
| 5,411,023 A | 5/1995 | Morris, Sr. et al. | 5,645,060 A | 7/1997 | Yorkey et al. |
| 5,411,024 A | 5/1995 | Thomas et al. | 5,645,440 A | 7/1997 | Tobler et al. |
| 5,413,099 A | 5/1995 | Schmidt et al. | 5,660,567 A | 8/1997 | Nierlich et al. |
| 5,413,100 A | 5/1995 | Barthelemy et al. | 5,662,105 A | 9/1997 | Tien |
| 5,413,101 A | 5/1995 | Sugiura | 5,662,106 A | 9/1997 | Swedlow et al. |
| 5,413,102 A | 5/1995 | Schmidt et al. | 5,664,270 A | 9/1997 | Bell et al. |
| 5,417,207 A | 5/1995 | Young et al. | 5,666,952 A | 9/1997 | Fuse et al. |
| 5,421,329 A | 6/1995 | Casciani et al. | 5,671,529 A | 9/1997 | Nelson |
| 5,425,360 A | 6/1995 | Nelson | 5,673,692 A | 10/1997 | Schulze et al. |
| 5,425,362 A | 6/1995 | Siker et al. | 5,673,693 A | 10/1997 | Solenberger |
| 5,427,093 A | 6/1995 | Ogawa et al. | 5,676,139 A | 10/1997 | Goldberger et al. |
| 5,429,128 A | 7/1995 | Cadell et al. | 5,676,141 A | 10/1997 | Hollub |
| 5,429,129 A | 7/1995 | Lovejoy et al. | 5,678,544 A | 10/1997 | DeLonzor et al. |
| 5,431,159 A | 7/1995 | Baker et al. | 5,680,857 A | 10/1997 | Pelikan et al. |
| 5,431,170 A | 7/1995 | Mathews | 5,685,299 A | 11/1997 | Diab et al. |
| 5,437,275 A | 8/1995 | Amundsen et al. | 5,685,301 A | 11/1997 | Klomhaus |
| 5,438,986 A | 8/1995 | Disch et al. | 5,687,719 A | 11/1997 | Sato et al. |
| 5,448,991 A | 9/1995 | Polson et al. | 5,687,722 A | 11/1997 | Tien et al. |
| 5,452,717 A | 9/1995 | Branigan et al. | 5,692,503 A | 12/1997 | Kuenstner |
| 5,465,714 A | 11/1995 | Scheuing | 5,692,505 A | 12/1997 | Fouts |
| 5,469,845 A | 11/1995 | DeLonzor et al. | 5,709,205 A | 1/1998 | Bukta |
| RE035,122 E | 12/1995 | Corenman et al. | 5,713,355 A | 2/1998 | Richardson et al. |
| 5,482,034 A | 1/1996 | Lewis et al. | 5,724,967 A | 3/1998 | Venkatachalam |
| 5,482,036 A | 1/1996 | Diab et al. | 5,727,547 A | 3/1998 | Levinson et al. |
| 5,485,847 A | 1/1996 | Baker, Jr. | 5,730,124 A | 3/1998 | Yamauchi |
| 5,490,505 A | 2/1996 | Diab et al. | 5,731,582 A | 3/1998 | West |
| 5,490,523 A | 2/1996 | Isaacson et al. | D393,830 S | 4/1998 | Tobler et al. |
| 5,491,299 A | 2/1996 | Naylor et al. | 5,743,260 A | 4/1998 | Chung et al. |
| 5,494,032 A | 2/1996 | Robinson et al. | 5,743,262 A | 4/1998 | Lepper, Jr. et al. |
| 5,494,043 A | 2/1996 | O'Sullivan et al. | 5,743,263 A | 4/1998 | Baker, Jr. |
| 5,497,771 A | 3/1996 | Rosenheimer | 5,746,206 A | 5/1998 | Mannheimer |
| 5,499,627 A | 3/1996 | Steuer et al. | 5,746,697 A | 5/1998 | Swedlow et al. |
| 5,503,148 A | 4/1996 | Pologe et al. | 5,752,914 A | 5/1998 | Delonzor et al. |
| 5,505,199 A | 4/1996 | Kim | 5,755,226 A | 5/1998 | Carim et al. |
| 5,507,286 A | 4/1996 | Solenberger | 5,758,644 A | 6/1998 | Diab et al. |
| 5,511,546 A | 4/1996 | Hon | 5,760,910 A | 6/1998 | Lepper, Jr. et al. |
| 5,517,988 A | 5/1996 | Gerhard | 5,766,125 A | 6/1998 | Aoyagi et al. |
| 5,520,177 A | 5/1996 | Ogawa et al. | 5,766,127 A | 6/1998 | Pologe et al. |
| 5,521,851 A | 5/1996 | Wei et al. | 5,769,785 A | 6/1998 | Diab et al. |
| 5,522,388 A | 6/1996 | Ishikawa et al. | 5,772,587 A | 6/1998 | Gratton et al. |
| 5,524,617 A | 6/1996 | Mannheimer | 5,774,213 A | 6/1998 | Trebino et al. |
| 5,529,064 A | 6/1996 | Rall et al. | 5,776,058 A | 7/1998 | Levinson et al. |
| 5,533,507 A | 7/1996 | Potratz et al. | 5,776,059 A | 7/1998 | Kaestle |
| 5,551,423 A | 9/1996 | Sugiura | 5,779,630 A | 7/1998 | Fein et al. |
| 5,551,424 A | 9/1996 | Morrison et al. | 5,779,631 A | 7/1998 | Chance |
| 5,553,614 A | 9/1996 | Chance | 5,782,237 A | 7/1998 | Casciani et al. |
| 5,553,615 A | 9/1996 | Carim et al. | 5,782,756 A | 7/1998 | Mannheimer |
| 5,555,882 A | 9/1996 | Richardson et al. | 5,782,757 A | 7/1998 | Diab et al. |
| 5,558,096 A | 9/1996 | Palatnik | 5,782,758 A | 7/1998 | Ausec et al. |
| 5,560,355 A | 10/1996 | Merchant et al. | 5,786,592 A | 7/1998 | Hök |
| 5,564,417 A | 10/1996 | Chance | 5,788,634 A | 8/1998 | Suda et al. |
| 5,575,284 A | 11/1996 | Athan et al. | 5,790,729 A | 8/1998 | Pologe et al. |
| 5,575,285 A | 11/1996 | Takanashi et al. | 5,792,052 A | 8/1998 | Isaacson et al. |

| | | | | | | |
|---|---|---|---|---|---|---|
| 5,795,292 A | 8/1998 | Lewis et al. | | 5,987,343 A | 11/1999 | Kinast |
| 5,797,841 A | 8/1998 | DeLonzor et al. | | 5,991,648 A | 11/1999 | Levin |
| 5,800,348 A | 9/1998 | Kaestle | | 5,995,855 A | 11/1999 | Kiani et al. |
| 5,800,349 A | 9/1998 | Isaacson et al. | | 5,995,856 A | 11/1999 | Mannheimer et al. |
| 5,803,910 A | 9/1998 | Potratz | | 5,995,858 A | 11/1999 | Kinast |
| 5,807,246 A | 9/1998 | Sakaguchi et al. | | 5,995,859 A | 11/1999 | Takahashi |
| 5,807,247 A | 9/1998 | Merchant et al. | | 5,997,343 A | 12/1999 | Mills et al. |
| 5,807,248 A | 9/1998 | Mills | | 5,999,834 A | 12/1999 | Wang et al. |
| 5,810,723 A | 9/1998 | Aldrich | | 6,002,952 A | 12/1999 | Diab et al. |
| 5,810,724 A | 9/1998 | Gronvall | | 6,005,658 A | 12/1999 | Kaluza et al. |
| 5,813,980 A | 9/1998 | Levinson et al. | | 6,006,120 A | 12/1999 | Levin |
| 5,817,008 A | 10/1998 | Rafert et al. | | 6,011,985 A | 1/2000 | Athan et al. |
| 5,817,009 A | 10/1998 | Rosenheimer et al. | | 6,011,986 A | 1/2000 | Diab et al. |
| 5,817,010 A | 10/1998 | Hibl | | 6,014,576 A | 1/2000 | Raley et al. |
| 5,818,985 A | 10/1998 | Merchant et al. | | 6,018,673 A | 1/2000 | Chin et al. |
| 5,820,550 A | 10/1998 | Polson et al. | | 6,018,674 A | 1/2000 | Aronow |
| 5,823,950 A | 10/1998 | Diab et al. | | 6,022,321 A | 2/2000 | Amano et al. |
| 5,823,952 A | 10/1998 | Levinson et al. | | 6,023,541 A | 2/2000 | Merchant et al. |
| 5,827,179 A | 10/1998 | Lichter et al. | | 6,026,312 A | 2/2000 | Shemwell et al. |
| 5,827,182 A | 10/1998 | Raley et al. | | 6,026,314 A | 2/2000 | Amerov et al. |
| 5,829,439 A | 11/1998 | Yokosawa et al. | | 6,031,603 A | 2/2000 | Fine et al. |
| 5,830,135 A | 11/1998 | Bosque et al. | | 6,035,223 A | 3/2000 | Baker, Jr. |
| 5,830,136 A | 11/1998 | DeLonzor et al. | | 6,036,642 A | 3/2000 | Diab et al. |
| 5,830,137 A | 11/1998 | Scharf | | 6,041,247 A | 3/2000 | Weckstrom et al. |
| 5,839,439 A | 11/1998 | Nierlich et al. | | 6,044,283 A | 3/2000 | Fein et al. |
| RE036,000 E | 12/1998 | Swedlow et al. | | 6,047,201 A | 4/2000 | Jackson, III |
| 5,842,979 A | 12/1998 | Jarman et al. | | 6,055,447 A | 4/2000 | Well |
| 5,842,981 A | 12/1998 | Larsen et al. | | 6,061,584 A | 5/2000 | Lovejoy et al. |
| 5,842,982 A | 12/1998 | Mannheimer | | 6,064,898 A | 5/2000 | Aldrich |
| 5,846,190 A | 12/1998 | Woehrle | | 6,064,899 A | 5/2000 | Fein et al. |
| 5,851,178 A | 12/1998 | Aronow | | 6,067,462 A | 5/2000 | Diab et al. |
| 5,851,179 A | 12/1998 | Ritson et al. | | 6,073,038 A | 6/2000 | Wang et al. |
| 5,853,364 A | 12/1998 | Baker, Jr. et al. | | 6,078,829 A | 6/2000 | Uchida |
| 5,860,919 A | 1/1999 | Kiani-Azarbayjany et al. | | 6,078,833 A | 6/2000 | Hueber |
| 5,865,736 A | 2/1999 | Baker, Jr. et al. | | 6,081,735 A | 6/2000 | Diab et al. |
| 5,879,294 A | 3/1999 | Anderson et al. | | 6,083,157 A | 7/2000 | Noller |
| 5,885,213 A | 3/1999 | Richardson et al. | | 6,083,172 A | 7/2000 | Baker, Jr. et al. |
| 5,890,929 A | 4/1999 | Mills et al. | | 6,088,607 A | 7/2000 | Diab et al. |
| 5,891,021 A | 4/1999 | Dillon et al. | | 6,094,592 A | 7/2000 | Yorkey et al. |
| 5,891,022 A | 4/1999 | Pologe | | 6,095,974 A | 8/2000 | Shemwell et al. |
| 5,891,024 A | 4/1999 | Jarman et al. | | 6,104,938 A | 8/2000 | Huiku et al. |
| 5,891,025 A | 4/1999 | Buschmann et al. | | 6,104,939 A | 8/2000 | Groner |
| 5,891,026 A | 4/1999 | Wang et al. | | 6,112,107 A | 8/2000 | Hannula |
| 5,902,235 A | 5/1999 | Lewis et al. | | 6,113,541 A | 9/2000 | Dias et al. |
| 5,910,108 A | 6/1999 | Solenberger | | 6,115,621 A | 9/2000 | Chin |
| 5,911,690 A | 6/1999 | Rall | | 6,122,535 A | 9/2000 | Kaestle et al. |
| 5,912,656 A | 6/1999 | Tham et al. | | 6,133,994 A | 10/2000 | Mathews et al. |
| 5,913,819 A | 6/1999 | Taylor et al. | | 6,135,952 A | 10/2000 | Coetzee |
| 5,916,154 A | 6/1999 | Hobbs et al. | | 6,144,444 A | 11/2000 | Haworth et al. |
| 5,916,155 A | 6/1999 | Levinson et al. | | 6,144,867 A | 11/2000 | Walker et al. |
| 5,919,133 A | 7/1999 | Taylor et al. | | 6,144,868 A | 11/2000 | Parker |
| 5,919,134 A | 7/1999 | Diab | | 6,149,481 A | 11/2000 | Wang et al. |
| 5,920,263 A | 7/1999 | Huttenhoff et al. | | 6,151,107 A | 11/2000 | Schöllermann et al. |
| 5,921,921 A | 7/1999 | Potratz et al. | | 6,151,516 A | 11/2000 | Kiani-Azarbayjany et al. |
| 5,922,607 A | 7/1999 | Bernreuter | | 6,151,518 A | 11/2000 | Hayashi |
| 5,924,979 A | 7/1999 | Swedlow et al. | | 6,152,754 A | 11/2000 | Gerhardt et al. |
| 5,924,980 A | 7/1999 | Coetzee | | 6,154,667 A | 11/2000 | Miura et al. |
| 5,924,982 A | 7/1999 | Chin | | 6,157,850 A | 12/2000 | Diab et al. |
| 5,924,985 A | 7/1999 | Jones | | 6,159,147 A | 12/2000 | Lichter et al. |
| 5,934,277 A | 8/1999 | Mortz | | 6,163,715 A | 12/2000 | Larsen et al. |
| 5,934,925 A | 8/1999 | Tobler et al. | | 6,165,005 A | 12/2000 | Mills et al. |
| 5,940,182 A | 8/1999 | Lepper, Jr. et al. | | 6,173,196 B1 | 1/2001 | Delonzor et al. |
| 5,954,644 A | 9/1999 | Dettling et al. | | 6,178,343 B1 | 1/2001 | Bindszus et al. |
| 5,957,840 A | 9/1999 | Terasawa et al. | | 6,179,159 B1 | 1/2001 | Gurley |
| 5,960,610 A | 10/1999 | Levinson et al. | | 6,181,958 B1 | 1/2001 | Steuer et al. |
| 5,961,450 A | 10/1999 | Merchant et al. | | 6,181,959 B1 | 1/2001 | Schöllermann et al. |
| 5,961,452 A | 10/1999 | Chung et al. | | 6,184,521 B1 | 2/2001 | Coffin, IV et al. |
| 5,964,701 A | 10/1999 | Asada et al. | | 6,188,470 B1 | 2/2001 | Grace |
| 5,971,930 A | 10/1999 | Elghazzawi | | 6,192,260 B1 | 2/2001 | Chance |
| 5,978,691 A | 11/1999 | Mills | | 6,195,575 B1 | 2/2001 | Levinson |
| 5,978,693 A | 11/1999 | Hamilton et al. | | 6,198,951 B1 | 3/2001 | Kosuda et al. |
| 5,983,120 A | 11/1999 | Groner et al. | | 6,206,830 B1 | 3/2001 | Diab et al. |
| 5,983,122 A | 11/1999 | Jarman et al. | | 6,213,952 B1 | 4/2001 | Finarov et al. |

| | | | | | | |
|---|---|---|---|---|---|---|
| 6,217,523 | B1 | 4/2001 | Amano et al. | 6,438,396 | B1 | 8/2002 | Cook |
| 6,222,189 | B1 | 4/2001 | Misner et al. | 6,438,399 | B1 | 8/2002 | Kurth |
| 6,223,064 | B1 | 4/2001 | Lynn | 6,449,501 | B1 | 9/2002 | Reuss |
| 6,226,539 | B1 | 5/2001 | Potratz | 6,453,183 | B1 | 9/2002 | Walker |
| 6,226,540 | B1 | 5/2001 | Bernreuter et al. | 6,453,184 | B1 | 9/2002 | Hyogo et al. |
| 6,229,856 | B1 | 5/2001 | Diab et al. | 6,456,862 | B2 | 9/2002 | Benni |
| 6,230,035 | B1 | 5/2001 | Aoyagi et al. | 6,461,305 | B1 | 10/2002 | Schnall |
| 6,233,470 | B1 | 5/2001 | Tsuchiya | 6,463,310 | B1 | 10/2002 | Swedlow et al. |
| 6,236,871 | B1 | 5/2001 | Tsuchiya | 6,463,311 | B1 | 10/2002 | Diab |
| 6,236,872 | B1 | 5/2001 | Diab et al. | 6,466,808 | B1 | 10/2002 | Chin et al. |
| 6,240,305 | B1 | 5/2001 | Tsuchiya | 6,466,809 | B1 | 10/2002 | Riley |
| 6,253,097 | B1 | 6/2001 | Aronow et al. | 6,470,199 | B1 | 10/2002 | Kopotic et al. |
| 6,253,098 | B1 | 6/2001 | Walker et al. | 6,470,200 | B2 | 10/2002 | Walker et al. |
| 6,256,523 | B1 | 7/2001 | Diab et al. | 6,480,729 | B2 | 11/2002 | Stone |
| 6,256,524 | B1 | 7/2001 | Walker et al. | 6,490,466 | B1 | 12/2002 | Fein et al. |
| 6,261,236 | B1 | 7/2001 | Grinblatov | 6,493,568 | B1 | 12/2002 | Bell |
| 6,263,221 | B1 | 7/2001 | Chance et al. | 6,496,711 | B1 | 12/2002 | Athan et al. |
| 6,263,222 | B1 | 7/2001 | Diab et al. | 6,498,942 | B1 | 12/2002 | Esenaliev et al. |
| 6,263,223 | B1 | 7/2001 | Sheperd et al. | 6,501,974 | B2 | 12/2002 | Huiku |
| 6,266,546 | B1 | 7/2001 | Steuer et al. | 6,501,975 | B2 | 12/2002 | Diab et al. |
| 6,266,547 | B1 | 7/2001 | Walker et al. | 6,505,060 | B1 | 1/2003 | Norris |
| 6,272,363 | B1 | 8/2001 | Casciani et al. | 6,505,061 | B2 | 1/2003 | Larson |
| 6,278,522 | B1 | 8/2001 | Lepper, Jr. et al. | 6,505,133 | B1 | 1/2003 | Hanna et al. |
| 6,280,213 | B1 | 8/2001 | Tobler et al. | 6,510,329 | B2 | 1/2003 | Heckel |
| 6,280,381 | B1 | 8/2001 | Malin et al. | 6,510,331 | B1 | 1/2003 | Williams et al. |
| 6,285,894 | B1 | 9/2001 | Oppelt et al. | 6,512,937 | B2 | 1/2003 | Blank et al. |
| 6,285,895 | B1 | 9/2001 | Ristolainen et al. | 6,515,273 | B2 | 2/2003 | Al-Ali |
| 6,285,896 | B1 | 9/2001 | Tobler et al. | 6,519,484 | B1 | 2/2003 | Lovejoy et al. |
| 6,298,252 | B1 | 10/2001 | Kovach et al. | 6,519,486 | B1 | 2/2003 | Edgar, Jr. et al. |
| 6,308,089 | B1 | 10/2001 | Von der Ruhr et al. | 6,519,487 | B1 | 2/2003 | Parker |
| 6,321,100 | B1 | 11/2001 | Parker | 6,525,386 | B1 | 2/2003 | Mills et al. |
| 6,330,468 | B1 | 12/2001 | Scharf | 6,526,300 | B1 | 2/2003 | Kiani et al. |
| 6,334,065 | B1 | 12/2001 | Al-Ali et al. | 6,526,301 | B2 | 2/2003 | Larsen et al. |
| 6,339,715 | B1 | 1/2002 | Bahr et al. | 6,541,756 | B2 | 4/2003 | Schulz et al. |
| 6,342,039 | B1 | 1/2002 | Lynn | 6,542,764 | B1 | 4/2003 | Al-Ali et al. |
| 6,343,223 | B1 | 1/2002 | Chin et al. | 6,546,267 | B1 | 4/2003 | Sugiura et al. |
| 6,343,224 | B1 | 1/2002 | Parker | 6,553,241 | B2 | 4/2003 | Mannheimer et al. |
| 6,349,228 | B1 | 2/2002 | Kiani et al. | 6,553,242 | B1 | 4/2003 | Sarussi |
| 6,351,658 | B1 | 2/2002 | Middleman et al. | 6,553,243 | B2 | 4/2003 | Gurley |
| 6,353,750 | B1 | 3/2002 | Kimura | 6,554,788 | B1 | 4/2003 | Hunley |
| 6,356,774 | B1 | 3/2002 | Bernstein et al. | 6,556,852 | B1 | 4/2003 | Schulze et al. |
| 6,360,113 | B1 | 3/2002 | Dettling | 6,560,470 | B1 | 5/2003 | Pologe |
| 6,360,114 | B1 | 3/2002 | Diab et al. | 6,564,077 | B2 | 5/2003 | Mortara |
| 6,361,501 | B1 | 3/2002 | Amano et al. | 6,564,088 | B1 | 5/2003 | Soller et al. |
| 6,363,269 | B1 | 3/2002 | Hanna et al. | 6,571,113 | B1 | 5/2003 | Fein et al. |
| D455,834 | S | 4/2002 | Donars et al. | 6,571,114 | B1 | 5/2003 | Koike et al. |
| 6,370,408 | B1 | 4/2002 | Merchant et al. | 6,574,491 | B2 | 6/2003 | Elghazzawi |
| 6,370,409 | B1 | 4/2002 | Chung et al. | 6,580,086 | B1 | 6/2003 | Schulz et al. |
| 6,371,921 | B1 | 4/2002 | Caro | 6,584,336 | B1 | 6/2003 | Ali et al. |
| 6,374,129 | B1 | 4/2002 | Chin et al. | 6,587,703 | B2 | 7/2003 | Cheng et al. |
| 6,377,829 | B1 | 4/2002 | Al-Ali et al. | 6,587,704 | B1 | 7/2003 | Fine et al. |
| 6,381,479 | B1 | 4/2002 | Norris | 6,589,172 | B2 | 7/2003 | Williams et al. |
| 6,381,480 | B1 | 4/2002 | Stoddar et al. | 6,591,122 | B2 | 7/2003 | Schmitt |
| 6,385,471 | B1 | 5/2002 | Mortz | 6,591,123 | B2 | 7/2003 | Fein et al. |
| 6,385,821 | B1 | 5/2002 | Modgil et al. | 6,594,511 | B2 | 7/2003 | Stone et al. |
| 6,388,240 | B2 | 5/2002 | Schulz et al. | 6,594,512 | B2 | 7/2003 | Huang |
| 6,393,310 | B1 | 5/2002 | Kuenster | 6,594,513 | B1 | 7/2003 | Jobsis et al. |
| 6,393,311 | B1 | 5/2002 | Edgar, Jr. et al. | 6,597,931 | B1 | 7/2003 | Cheng et al. |
| 6,397,091 | B2 | 5/2002 | Diab et al. | 6,597,933 | B2 | 7/2003 | Kiani et al. |
| 6,397,092 | B1 | 5/2002 | Norris et al. | 6,600,940 | B1 | 7/2003 | Fein et al. |
| 6,397,093 | B1 | 5/2002 | Aldrich | 6,606,510 | B2 | 8/2003 | Swedlow et al. |
| 6,400,971 | B1 | 6/2002 | Finarov et al. | 6,606,511 | B1 | 8/2003 | Ali et al. |
| 6,400,972 | B1 | 6/2002 | Fine | 6,606,512 | B2 | 8/2003 | Muz et al. |
| 6,400,973 | B1 | 6/2002 | Winter | 6,608,562 | B1 | 8/2003 | Kimura et al. |
| 6,402,690 | B1 | 6/2002 | Rhee et al. | 6,609,016 | B1 | 8/2003 | Lynn |
| 6,408,198 | B1 | 6/2002 | Hanna et al. | 6,615,064 | B1 | 9/2003 | Aldrich |
| 6,411,832 | B1 | 6/2002 | Guthermann | 6,615,065 | B1 | 9/2003 | Barrett et al. |
| 6,411,833 | B1 | 6/2002 | Baker, Jr. et al. | 6,618,602 | B2 | 9/2003 | Levin |
| 6,421,549 | B1 | 7/2002 | Jacques | 6,622,034 | B1 | 9/2003 | Gorski et al. |
| 6,430,423 | B2 | 8/2002 | DeLonzor et al. | 6,628,975 | B1 | 9/2003 | Fein et al. |
| 6,430,513 | B1 | 8/2002 | Wang et al. | 6,631,281 | B1 | 10/2003 | Kästle |
| 6,430,525 | B1 | 8/2002 | Weber et al. | 6,632,181 | B2 | 10/2003 | Flaherty |
| 6,434,408 | B1 | 8/2002 | Heckel et al. | 6,640,116 | B2 | 10/2003 | Diab |

| | | |  | | | |
|---|---|---|---|---|---|---|
| 6,643,530 | B2 | 11/2003 | Diab et al. | 6,773,397 | B2 | 8/2004 | Kelly |
| 6,643,531 | B1 | 11/2003 | Katarow | 6,778,923 | B2 | 8/2004 | Norris et al. |
| 6,647,279 | B2 | 11/2003 | Pologe | 6,780,158 | B2 | 8/2004 | Yarita |
| 6,647,280 | B2 | 11/2003 | Bahr et al. | 6,791,689 | B1 | 9/2004 | Weckstrom |
| 6,650,916 | B2 | 11/2003 | Cook | 6,792,300 | B1 | 9/2004 | Diab et al. |
| 6,650,917 | B2 | 11/2003 | Diab et al. | 6,801,797 | B2 | 10/2004 | Mannheimer et al. |
| 6,650,918 | B2 | 11/2003 | Terry | 6,801,798 | B2 | 10/2004 | Geddes et al. |
| 6,654,621 | B2 | 11/2003 | Palatnik et al. | 6,801,799 | B2 | 10/2004 | Mendelson |
| 6,654,622 | B1 | 11/2003 | Eberhard et al. | 6,801,802 | B2 | 10/2004 | Sitzman et al. |
| 6,654,623 | B1 | 11/2003 | Kästle | 6,802,812 | B1 | 10/2004 | Walker et al. |
| 6,654,624 | B2 | 11/2003 | Diab et al. | 6,805,673 | B2 | 10/2004 | Dekker |
| 6,658,276 | B2 | 12/2003 | Kianl et al. | 6,810,277 | B2 | 10/2004 | Edgar, Jr. et al. |
| 6,658,277 | B2 | 12/2003 | Wassermann | 6,813,511 | B2 | 11/2004 | Diab et al. |
| 6,662,033 | B2 | 12/2003 | Casciani et al. | 6,816,741 | B2 | 11/2004 | Diab |
| 6,665,551 | B1 | 12/2003 | Suzuki | 6,819,950 | B2 | 11/2004 | Mills |
| 6,668,182 | B2 | 12/2003 | Hubelbank | 6,822,564 | B2 | 11/2004 | Al-Ali |
| 6,668,183 | B2 | 12/2003 | Hicks et al. | 6,825,619 | B2 | 11/2004 | Norris |
| 6,671,526 | B1 | 12/2003 | Aoyagi et al. | 6,826,419 | B2 | 11/2004 | Diab et al. |
| 6,671,528 | B2 | 12/2003 | Steuer et al. | 6,829,496 | B2 | 12/2004 | Nagai et al. |
| 6,671,530 | B2 | 12/2003 | Chung et al. | 6,830,711 | B2 | 12/2004 | Mills et al. |
| 6,671,531 | B2 | 12/2003 | Al-Ali et al. | 6,836,679 | B2 | 12/2004 | Baker, Jr. et al. |
| 6,671,532 | B1 | 12/2003 | Fudge et al. | 6,839,579 | B1 | 1/2005 | Chin |
| 6,675,031 | B1 | 1/2004 | Porges et al. | 6,839,580 | B2 | 1/2005 | Zonios et al. |
| 6,678,543 | B2 | 1/2004 | Diab et al. | 6,839,582 | B2 | 1/2005 | Heckel |
| 6,681,126 | B2 | 1/2004 | Solenberger | 6,839,659 | B2 | 1/2005 | Tarassenko et al. |
| 6,681,128 | B2 | 1/2004 | Steuer et al. | 6,842,635 | B1 | 1/2005 | Parker |
| 6,681,454 | B2 | 1/2004 | Modgil et al. | 6,845,256 | B2 | 1/2005 | Chin et al. |
| 6,684,090 | B2 | 1/2004 | Ali et al. | 6,850,787 | B2 | 2/2005 | Weber et al. |
| 6,684,091 | B2 | 1/2004 | Parker | 6,850,788 | B2 | 2/2005 | Al-Ali |
| 6,694,160 | B2 | 2/2004 | Chin | 6,850,789 | B2 | 2/2005 | Schweitzer, Jr. et al. |
| 6,697,653 | B2 | 2/2004 | Hanna | 6,861,639 | B2 | 3/2005 | Al-Ali |
| 6,697,655 | B2 | 2/2004 | Sueppel et al. | 6,863,652 | B2 | 3/2005 | Huang et al. |
| 6,697,656 | B1 | 2/2004 | Al-Ali | 6,865,407 | B2 | 3/2005 | Kimball et al. |
| 6,697,658 | B2 | 2/2004 | Al-Ali | 6,879,850 | B2 | 4/2005 | Kimball |
| RE038,476 | E | 3/2004 | Diab et al. | 6,882,874 | B2 | 4/2005 | Huiku |
| 6,699,194 | B1 | 3/2004 | Diab et al. | 6,898,452 | B2 | 5/2005 | Al-Ali et al. |
| 6,699,199 | B2 | 3/2004 | Asada et al. | 6,909,912 | B2 | 6/2005 | Melker et al. |
| 6,701,170 | B2 | 3/2004 | Stetson | 6,912,413 | B2 | 6/2005 | Rantala et al. |
| 6,702,752 | B2 | 3/2004 | Dekker | 6,920,345 | B2 | 7/2005 | Al-Ali et al. |
| 6,707,257 | B2 | 3/2004 | Norris | 6,931,269 | B2 | 8/2005 | Terry |
| 6,708,049 | B1 | 3/2004 | Berson et al. | 6,934,570 | B2 | 8/2005 | Kiani et al. |
| 6,709,402 | B2 | 3/2004 | Dekker | 6,941,162 | B2 | 9/2005 | Fudge et al. |
| 6,711,424 | B1 | 3/2004 | Fine et al. | 6,947,781 | B2 | 9/2005 | Asada et al. |
| 6,711,425 | B1 | 3/2004 | Reuss | 6,950,687 | B2 | 9/2005 | Al-Ali |
| 6,712,762 | B1 | 3/2004 | Lichter | 6,954,664 | B2 | 10/2005 | Sweitzer |
| 6,714,803 | B1 | 3/2004 | Mortz | 6,968,221 | B2 | 11/2005 | Rosenthal |
| 6,714,804 | B2 | 3/2004 | Al-Ali et al. | 6,979,812 | B2 | 12/2005 | Al-Ali |
| 6,714,805 | B2 | 3/2004 | Jeon et al. | 6,983,178 | B2 | 1/2006 | Fine et al. |
| RE038,492 | E | 4/2004 | Diab et al. | 6,985,763 | B2 | 1/2006 | Boas et al. |
| 6,719,686 | B2 | 4/2004 | Coakley et al. | 6,985,764 | B2 | 1/2006 | Mason et al. |
| 6,719,705 | B2 | 4/2004 | Mills | 6,990,426 | B2 | 1/2006 | Yoon et al. |
| 6,720,734 | B2 | 4/2004 | Norris | 6,992,751 | B2 | 1/2006 | Okita et al. |
| 6,721,584 | B2 | 4/2004 | Baker, Jr. et al. | 6,992,772 | B2 | 1/2006 | Block |
| 6,721,585 | B1 | 4/2004 | Parker | 6,993,371 | B2 | 1/2006 | Kiani et al. |
| 6,725,074 | B1 | 4/2004 | Kästle | 6,993,372 | B2 | 1/2006 | Fine et al. |
| 6,725,075 | B2 | 4/2004 | Al-Ali | 6,996,427 | B2 | 2/2006 | Ali et al. |
| 6,731,962 | B1 | 5/2004 | Katarow | 7,003,338 | B2 | 2/2006 | Weber et al. |
| 6,731,963 | B2 | 5/2004 | Finarov et al. | 7,003,339 | B2 | 2/2006 | Diab et al. |
| 6,731,967 | B1 | 5/2004 | Turcott | 7,006,855 | B1 | 2/2006 | Sarussi |
| 6,735,459 | B2 | 5/2004 | Parker | 7,006,856 | B2 | 2/2006 | Baker, Jr. et al. |
| 6,745,060 | B2 | 6/2004 | Diab et al. | 7,016,715 | B2 | 3/2006 | Stetson |
| 6,745,061 | B1 | 6/2004 | Hicks et al. | 7,020,507 | B2 | 3/2006 | Scharf et al. |
| 6,748,253 | B2 | 6/2004 | Norris et al. | 7,024,233 | B2 | 4/2006 | Ali et al. |
| 6,748,254 | B2 | 6/2004 | O'Neill et al. | 7,024,235 | B2 | 4/2006 | Melker et al. |
| 6,754,515 | B1 | 6/2004 | Pologe | 7,025,728 | B2 | 4/2006 | Ito et al. |
| 6,754,516 | B2 | 6/2004 | Mannheimer | 7,027,849 | B2 | 4/2006 | Al-Ali |
| 6,760,607 | B2 | 7/2004 | Al-Ali | 7,027,850 | B2 | 4/2006 | Wasserman |
| 6,760,609 | B2 | 7/2004 | Jacques | 7,039,449 | B2 | 5/2006 | Al-Ali |
| 6,760,610 | B2 | 7/2004 | Tscupp et al. | 7,043,289 | B2 | 5/2006 | Fine et al. |
| 6,763,255 | B2 | 7/2004 | DeLonzor et al. | 7,047,055 | B2 | 5/2006 | Boas et al. |
| 6,763,256 | B2 | 7/2004 | Kimball et al. | 7,060,035 | B2 | 6/2006 | Wasserman |
| 6,770,028 | B1 | 8/2004 | Ali et al. | 7,062,307 | B2 | 6/2006 | Norris et al. |
| 6,771,994 | B2 | 8/2004 | Kiani et al. | 7,067,893 | B2 | 6/2006 | Mills et al. |

| | | | | | | |
|---|---|---|---|---|---|---|
| 7,072,701 | B2 | 7/2006 | Chen et al. | 2004/0162472 A1 | 8/2004 | Berson et al. |
| 7,072,702 | B2 | 7/2006 | Edgar, Jr. et al. | 2004/0167381 A1 | 8/2004 | Lichter |
| 7,079,880 | B2 | 7/2006 | Stetson | 2004/0186358 A1 | 9/2004 | Chernow et al. |
| 7,085,597 | B2 | 8/2006 | Fein et al. | 2004/0204637 A1 | 10/2004 | Diab et al. |
| 7,096,052 | B2 | 8/2006 | Mason et al. | 2004/0204638 A1 | 10/2004 | Diab et al. |
| 7,096,054 | B2 | 8/2006 | Abdul-Hafiz et al. | 2004/0204639 A1 | 10/2004 | Casciani et al. |
| 7,107,088 | B2 | 9/2006 | Aceti | 2004/0204865 A1 | 10/2004 | Lee et al. |
| 7,113,815 | B2 | 9/2006 | O'Neil et al. | 2004/0210146 A1 | 10/2004 | Diab et al. |
| 7,123,950 | B2 | 10/2006 | Mannheimer | 2004/0215085 A1 | 10/2004 | Schnall |
| 7,130,671 | B2 | 10/2006 | Baker, Jr. et al. | 2004/0236196 A1 | 11/2004 | Diab et al. |
| 7,132,641 | B2 | 11/2006 | Schulz et al. | 2005/0004479 A1 | 1/2005 | Townsend et al. |
| 7,133,711 | B2 | 11/2006 | Chernoguz et al. | 2005/0014999 A1 | 1/2005 | Rahe-Meyer |
| 7,139,559 | B2 | 11/2006 | Kenagy et al. | 2005/0020887 A1 | 1/2005 | Goldberg |
| 7,142,901 | B2 | 11/2006 | Kiani et al. | 2005/0033131 A1 | 2/2005 | Chen |
| 7,127,278 | B2 | 12/2006 | Melker et al. | 2005/0043599 A1 | 2/2005 | O'Mara |
| 7,162,288 | B2 | 1/2007 | Nordstrom et al. | 2005/0043600 A1 | 2/2005 | Diab et al. |
| 7,190,987 | B2 | 3/2007 | Kindekugel et al. | 2005/0049468 A1 | 3/2005 | Carlson |
| 7,198,778 | B2 | 4/2007 | Achilefu et al. | 2005/0070773 A1 | 3/2005 | Chin |
| 7,215,984 | B2 | 5/2007 | Diab et al. | 2005/0075546 A1 | 4/2005 | Samsoondar |
| 7,225,007 | B2 | 5/2007 | Al-Ali et al. | 2005/0075550 A1 | 4/2005 | Lindekugel |
| 7,228,161 | B2 | 6/2007 | Chin | 2005/0085704 A1 | 4/2005 | Schulz |
| 7,236,811 | B2 | 6/2007 | Schmitt et al. | 2005/0090720 A1 | 4/2005 | Wu |
| 7,248,910 | B2 | 7/2007 | Li et al. | 2005/0197548 A1 | 9/2005 | Dietiker |
| 7,254,433 | B2 | 8/2007 | Diab et al. | 2005/0228248 A1 | 10/2005 | Dietiker |
| 7,254,434 | B2 | 8/2007 | Schulz et al. | 2005/0256386 A1 | 11/2005 | Chan |
| 7,280,858 | B2 | 10/2007 | Al-Ali et al. | 2005/0272986 A1 | 12/2005 | Smith |
| 7,295,866 | B2 | 11/2007 | Al-Ali | 2005/0277819 A1 | 12/2005 | Kiani et al. |
| 7,305,262 | B2 | 12/2007 | Brodnick et al. | 2006/0020179 A1 | 1/2006 | Anderson |
| 7,313,427 | B2 | 12/2007 | Benni | 2006/0030764 A1 | 2/2006 | Porges |
| 7,315,753 | B2 | 1/2008 | Baker, Jr. et al. | 2006/0058594 A1 | 3/2006 | Ishizuka et al. |
| 7,369,886 | B2 | 5/2008 | DeLonzor et al. | 2006/0074280 A1 | 4/2006 | Martis |
| 7,373,188 | B2 | 5/2008 | DeLonzor et al. | 2006/0084852 A1 | 4/2006 | Mason et al. |
| 7,373,189 | B2 | 5/2008 | DeLonzor et al. | 2006/0084878 A1 | 4/2006 | Banet |
| 7,373,190 | B2 | 5/2008 | DeLonzor et al. | 2006/0089547 A1 | 4/2006 | Sarussi |
| 7,373,191 | B2 | 5/2008 | DeLonzor et al. | 2006/0106294 A1 | 5/2006 | Maser et al. |
| 7,389,130 | B2 | 6/2008 | DeLonzor et al. | 2006/0122517 A1 | 6/2006 | Banet |
| 7,561,905 | B2 | 7/2009 | DeLonzor et al. | 2006/0129039 A1 | 6/2006 | Lindner |
| 2002/0016537 | A1 | 2/2002 | Muz et al. | 2006/0155198 A1 | 7/2006 | Schmid |
| 2002/0026109 | A1 | 2/2002 | Diab et al. | 2006/0173257 A1 | 8/2006 | Nagai |
| 2002/0028990 | A1 | 3/2002 | Shepherd et al. | 2006/0229508 A1 * | 10/2006 | Kermani et al. ............. 600/310 |
| 2002/0038078 | A1 | 3/2002 | Ito | 2007/0032710 A1 | 2/2007 | Raridan et al. |
| 2002/0042558 | A1 | 4/2002 | Mendelson | 2007/0032712 A1 | 2/2007 | Raridan et al. |
| 2002/0068859 | A1 | 6/2002 | Knopp | 2007/0032715 A1 | 2/2007 | Eghbal et al. |
| 2002/0072681 | A1 | 6/2002 | Schnall | 2007/0060808 A1 | 3/2007 | Hoarau |
| 2002/0103423 | A1 * | 8/2002 | Chin et al. .................. 600/322 | 2007/0073117 A1 | 3/2007 | Raridan |
| 2002/0116797 | A1 | 8/2002 | Modgil et al. | 2007/0073121 A1 | 3/2007 | Hoarau et al. |
| 2002/0128544 | A1 | 9/2002 | Diab et al. | 2007/0073122 A1 | 3/2007 | Hoarau |
| 2002/0133067 | A1 | 9/2002 | Jackson, III | 2007/0073123 A1 | 3/2007 | Raridan |
| 2002/0156354 | A1 | 10/2002 | Larson | 2007/0073125 A1 | 3/2007 | Hoarau et al. |
| 2002/0173706 | A1 | 11/2002 | Takatani | 2007/0073126 A1 | 3/2007 | Raridan |
| 2002/0190863 | A1 | 12/2002 | Lynn | 2007/0073128 A1 | 3/2007 | Hoarau |
| 2003/0018243 | A1 | 1/2003 | Gerhardt et al. | 2007/0078315 A1 | 4/2007 | Kling et al. |
| 2003/0036690 | A1 | 2/2003 | Geddes et al. | 2007/0078316 A1 | 4/2007 | Hoarau |
| 2003/0045785 | A1 | 3/2003 | Diab et al. | 2007/0260129 A1 | 11/2007 | Chin |
| 2003/0073889 | A1 | 4/2003 | Keilbach et al. | 2007/0260130 A1 | 11/2007 | Chin |
| 2003/0073890 | A1 | 4/2003 | Hanna | 2007/0260131 A1 | 11/2007 | Chin |
| 2003/0100840 | A1 | 5/2003 | Sugiura et al. | 2007/0299328 A1 | 12/2007 | Chin et al. |
| 2003/0187337 | A1 | 10/2003 | Tarassenko et al. | | | |
| 2003/0197679 | A1 | 10/2003 | Ali et al. | FOREIGN PATENT DOCUMENTS | | |
| 2003/0212316 | A1 | 11/2003 | Leiden et al. | | | |
| 2003/0225323 | A1 | 12/2003 | Kiani et al. | DE | 3516338 | 11/1986 |
| 2004/0006261 | A1 | 1/2004 | Swedlow et al. | DE | 3703458 | 8/1988 |
| 2004/0024326 | A1 | 2/2004 | Yeo et al. | DE | 3938759 | 5/1991 |
| 2004/0039272 | A1 | 2/2004 | Abdul-Hafiz et al. | DE | 4210102 | 9/1993 |
| 2004/0039273 | A1 | 2/2004 | Terry | DE | 4423597 | 8/1995 |
| 2004/0054291 | A1 | 3/2004 | Schulz et al. | DE | 19632361 | 2/1997 |
| 2004/0068164 | A1 | 4/2004 | Diab et al. | DE | 69123448 | 5/1997 |
| 2004/0092805 | A1 | 5/2004 | Yarita | DE | 19703220 | 7/1997 |
| 2004/0097797 | A1 | 5/2004 | Porges et al. | DE | 19640807 | 9/1997 |
| 2004/0098009 | A1 | 5/2004 | Boecker et al. | DE | 19647877 | 4/1998 |
| 2004/0117891 | A1 | 6/2004 | Hannula et al. | DE | 10030862 | 1/2002 |
| 2004/0147824 | A1 | 7/2004 | Diab et al. | DE | 20318882 | 4/2004 |
| 2004/0158134 | A1 | 8/2004 | Diab et al. | EP | 0127947 | 5/1984 |

| | | | | | | |
|---|---|---|---|---|---|---|
| EP | 00194105 | 9/1986 | | JP | 10216113 | 8/1998 |
| EP | 00204459 | 12/1986 | | JP | 10216114 | 8/1998 |
| EP | 0262779 | 4/1988 | | JP | 10216115 | 8/1998 |
| EP | 0315040 | 10/1988 | | JP | 10337282 | 12/1998 |
| EP | 0314331 | 5/1989 | | JP | 11019074 | 1/1999 |
| EP | 00352923 | 1/1990 | | JP | 11155841 | 6/1999 |
| EP | 0360977 | 4/1990 | | JP | 11188019 | 7/1999 |
| EP | 00430340 | 6/1991 | | JP | 11244268 | 9/1999 |
| EP | 0435500 | 7/1991 | | JP | 20107157 | 4/2000 |
| EP | 0572684 | 5/1992 | | JP | 20237170 | 9/2000 |
| EP | 00497021 | 8/1992 | | JP | 21245871 | 9/2001 |
| EP | 0529412 | 8/1992 | | JP | 22224088 | 8/2002 |
| EP | 0531631 | 9/1992 | | JP | 22282242 | 10/2002 |
| EP | 0566354 | 4/1993 | | JP | 23153881 | 5/2003 |
| EP | 0587009 | 8/1993 | | JP | 23153882 | 5/2003 |
| EP | 00630203 | 9/1993 | | JP | 23169791 | 6/2003 |
| EP | 0572684 | 12/1993 | | JP | 23194714 | 7/2003 |
| EP | 00615723 | 9/1994 | | JP | 23210438 | 7/2003 |
| EP | 00702931 | 3/1996 | | JP | 23275192 | 9/2003 |
| EP | 00724860 | 8/1996 | | JP | 23339678 | 12/2003 |
| EP | 00793942 | 9/1997 | | JP | 24008572 | 1/2004 |
| EP | 0864293 | 9/1998 | | JP | 24089546 | 3/2004 |
| EP | 01006863 | 10/1998 | | JP | 24113353 | 4/2004 |
| EP | 01006864 | 10/1998 | | JP | 24135854 | 5/2004 |
| EP | 0875199 | 11/1998 | | JP | 24148069 | 5/2004 |
| EP | 00998214 | 12/1998 | | JP | 24148070 | 5/2004 |
| EP | 0898933 | 3/1999 | | JP | 24159810 | 6/2004 |
| EP | 01332713 | 8/2003 | | JP | 24166775 | 6/2004 |
| EP | 01469773 | 8/2003 | | JP | 24194908 | 7/2004 |
| EP | 1502529 | 7/2004 | | JP | 24202190 | 7/2004 |
| EP | 01491135 | 12/2004 | | JP | 24248819 | 9/2004 |
| FR | 2685865 | 1/1992 | | JP | 24248820 | 9/2004 |
| GB | 2259545 | 3/1993 | | JP | 24261364 | 9/2004 |
| JP | 63275325 | 11/1988 | | JP | 24290412 | 10/2004 |
| JP | 2013450 | 1/1990 | | JP | 24290544 | 10/2004 |
| JP | 2111343 | 4/1990 | | JP | 24290545 | 10/2004 |
| JP | 02191434 | 7/1990 | | JP | 24329406 | 11/2004 |
| JP | 2237544 | 9/1990 | | JP | 24329607 | 11/2004 |
| JP | 3170866 | 7/1991 | | JP | 24329928 | 11/2004 |
| JP | 03173536 | 7/1991 | | JP | 24337605 | 12/2004 |
| JP | 3245042 | 10/1991 | | JP | 24344367 | 12/2004 |
| JP | 4174648 | 6/1992 | | JP | 24351107 | 12/2004 |
| JP | 4191642 | 7/1992 | | JP | 25034472 | 2/2005 |
| JP | 4332536 | 11/1992 | | WO | WO 90/01293 | 2/1990 |
| JP | 3124073 | 3/1993 | | WO | WO 90/04352 | 5/1990 |
| JP | 5049624 | 3/1993 | | WO | WO 91/01678 | 2/1991 |
| JP | 5049625 | 3/1993 | | WO | WO 91/11137 | 8/1991 |
| JP | 3115374 | 4/1993 | | WO | WO 92/00513 | 1/1992 |
| JP | 2005/200031 | 8/1993 | | WO | WO 92/21281 | 12/1992 |
| JP | 05200031 | 8/1993 | | WO | WO 93/09711 | 5/1993 |
| JP | 5212016 | 8/1993 | | WO | WO 93/13706 | 7/1993 |
| JP | 06014906 | 1/1994 | | WO | WO 93/16629 | 9/1993 |
| JP | 6016774 | 3/1994 | | WO | WO 94/03102 | 2/1994 |
| JP | 3116255 | 4/1994 | | WO | WO 94/23643 | 10/1994 |
| JP | 6029504 | 4/1994 | | WO | WO 95/02358 | 1/1995 |
| JP | 6098881 | 4/1994 | | WO | WO 95/12349 | 5/1995 |
| JP | 06154177 | 6/1994 | | WO | WO 95/16970 | 6/1995 |
| JP | 6269430 | 9/1994 | | WO | WO 96/13208 | 5/1996 |
| JP | 6285048 | 10/1994 | | WO | WO 96/39927 | 12/1996 |
| JP | 7001273 | 1/1995 | | WO | WO 97/36536 | 10/1997 |
| JP | 7124138 | 5/1995 | | WO | WO 97/36538 | 10/1997 |
| JP | 7136150 | 5/1995 | | WO | WO 97/49330 | 12/1997 |
| JP | 3116259 | 6/1995 | | WO | WO 98/09566 | 3/1998 |
| JP | 3116260 | 6/1995 | | WO | WO 98/17174 | 4/1998 |
| JP | 7155311 | 6/1995 | | WO | WO 98/18382 | 5/1998 |
| JP | 7155313 | 6/1995 | | WO | WO 98/43071 | 10/1998 |
| JP | 3238813 | 7/1995 | | WO | WO 98/51212 | 11/1998 |
| JP | 7171139 | 7/1995 | | WO | WO 98/57577 | 12/1998 |
| JP | 3134144 | 9/1995 | | WO | WO 99/00053 | 1/1999 |
| JP | 7236625 | 9/1995 | | WO | WO 99/32030 | 7/1999 |
| JP | 7246191 | 9/1995 | | WO | WO 99/47039 | 9/1999 |
| JP | 8256996 | 10/1996 | | WO | WO 99/63884 | 12/1999 |
| JP | 9192120 | 7/1997 | | WO | WO 00/21438 | 4/2000 |

| | | |
|---|---|---|
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 04/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |
| WO | WO 2006/104790 | 10/2006 |

OTHER PUBLICATIONS

U.S. Appl. No. 11/525,396, filed Sep. 22, 2006, Hoarau.
U.S. Appl. No. 11/525,635, filed Sep. 22, 2006, Hoarau.
U.S. Appl. No. 11/525,636, filed Sep. 22, 2006, Horau.
U.S. Appl. No. 11/525,693, filed Sep. 22, 2006, Hoarau.
U.S. Appl. No. 11/525,704, filed Sep. 22, 2006, Hoarau.
Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).
Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).
Aoyagi, T., et al.; "Analysis of Motion Artifacts in Pulse Oximetry," *Japanese Society ME*, vol. 42, p. 20 (1993) (Article in Japanese—contains English summary of article).
Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).
Vincente, L.M., et al.; "Adaptive Pre-Processing of Photoplethysmographic Blood Volume Pulse Measurements," pp. 114-117 (1996).
Plummer, John L., et al.; "Identification of Movement Artifact by the Nellcor N-200 and N-3000 Pulse Oximeters," *Journal of clinical Monitoring*, vol. 13, pp. 109-113 (1997).
Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).
Poets, C. F., et al.; "Detection of movement artifact in recorded pulse oximeter saturation," *Eur. J. Pediatr.*; vol. 156, pp. 808-811 (1997).
Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).
Nijland, Roel, et al.; "Validation of Reflectance Pulse Oximetry: an Evaluation of a new Sensor in Piglets," *Journal of Clinical Monitoring* vol. 13, pp. 43-49 (1997).
Soto, Denise A.; "A Comparative Study of Pulse Oximeter Measurements: Digit Versus Earlobe," Master of Science Thesis, California State University Dominguez Hills, May 1997, 46 pgs.
Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).
Izumi, Akio, et al.; "Accuracy and Utility of a New Reflectance Pulse Oximeter for Fetal Monitoring During Labor," *Journal of Clinical Monitoring*, vol. 13, pp. 103-108 (1997).
Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).
"Smaller Product, Tighter Tolerances Pose Dispensing Challenges for Medical Device Manufacturer," *Adhesives Age*, pp. 40-41 (Oct. 1997).
Buschman, J.P., et al.; "Principles and Problems of Calibration of Fetal Oximeters," *Biomedizinische Technik*, vol. 42, pp. 265-266 (1997).
Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.
Leahy, Martin J., et al.; "Sensor Validation in Biomedical Applications," *IFAC Modelling and Control in Biomedical Systems*, Warwick, UK; pp. 221-226 (1997).
Barreto, Armando B., et al.; "Adaptive LMS Delay Measurement in dual Blood Volume Pulse Signals for Non-Invasive Monitoring," *IEEE*, pp. 117-120 (1997).
Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.
DeKock, Marc; "Pulse Oximetry Probe Adhesive Disks: a Potential for Infant Aspiration," *Anesthesiology*, vol. 89, pp. 1603-1604 (1998).
East, Christine E., et al.; "Fetal Oxygen Saturation and Uterine Contractions During Labor," *American Journal of Perinatology*, vol. 15, No. 6, pp. 345-349 (Jun. 1998).
Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).
Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.
König, Volker, et al.; "Reflectance Pulse Oximetry—Principles and Obstetric Application in the Zurich System," *Journal of Clinical Monitoring and Computing*, vol. 14, pp. 403-412 (1998).
Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).
Hayes, Matthew J., et al.; "Quantitative evaluation of photoplethysmographic artifact reduction for pulse oximetry," *SPIE*, vol. 3570, pp. 138-147 (Sep. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor— Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved in Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku* (*Medical Technology*), vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisam, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo* (*Aritificial Respiration*), vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2$/$SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2$/$SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No, 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," Micromechatronics, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

\* cited by examiner

OPAQUE, ELECTRICALLY NONCONDUCTIVE REGION ON A MEDICAL SENSOR

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to certain aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry measures various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that emits light into a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount related to the amount of a particular constituent present in the blood. The amount of light absorbed and/or scattered may then be used to estimate the amount of the blood constituent in the tissue using various algorithms.

The pulse oximetry measurement depends in part on the assumption that the contribution of light that has not passed through a patient's tissue is negligible. However, outside light may leak into a sensor, causing detection of light that is not related to the amount of blood constituent present in the blood. Additionally, shunted light or light from a sensor's emitter, may be reflected around the exterior of the tissue and may be sensed by the detector without traveling first through the tissue. These light sources may cause measurement variations that result in erroneous blood constituent readings.

Some outside light infiltration into the sensor may be avoided by fitting the sensor snugly against the patient's tissue. However, such a conforming fit may be difficult to achieve over a broad range of patient physiologies without adjustment or excessive attention on the part of medical personnel. Additionally, an overly tight fit may cause local exsanguination of the tissue around the sensor. Exsanguinated tissue, which is devoid of blood, may shunt the sensor light through the tissue, which may also result in increased measurement errors.

External light and shunted light may also be prevented from reaching the sensor by certain coatings applied to the pulse oximetry device. For example, some sensors incorporate reflective coating on the tissue contacting surface to reflect shunted light away from the detector. However, these reflective materials are metal-based, and thus conductive, which may result in capacitive coupling between the emitter and detector. In particular, conductive reflective materials may provide electrical paths between the pulse oximeter's light emitter and the detector. These electrical paths may cause corruption of the detector's measurement signal, resulting in an incorrect reading of more or less absorption of light than is actually transmitted through the patient's tissue. Therefore, noise added to the signal by crosstalk can lead to erroneous physiological measurements.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; an emitter disposed on the sensor body, wherein the emitter is adapted to transmit light into tissue; a detector disposed on the sensor body, wherein the detector is adapted to detect the light; and at least one opaque region disposed on a tissue-contacting surface of the sensor body, the opaque region including a substantially electrically nonconductive material.

There is also provided a pulse oximetry system that includes a pulse oximetry monitor and a pulse oximetry sensor adapted to be operatively coupled to the monitor. The sensor includes: a sensor body; and at least one opaque region, the opaque region disposed on a tissue-contacting surface of the sensor body, including a substantially electrically nonconductive material.

There is also provided a method that includes: emitting light into tissue with an emitter; detecting the emitted light with a detector; absorbing light that has not been transmitted from the emitter through the tissue with at least one opaque region, wherein the at least one opaque region includes a substantially electrically nonconductive material; and measuring a physiological characteristic based on the detected light.

There is also provided a method of manufacturing a sensor that includes: providing a sensor body on which at least one sensing element is disposed; and providing at least one opaque region disposed on a tissue-contacting surface of the sensor body, the opaque region includes a nonconductive material.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
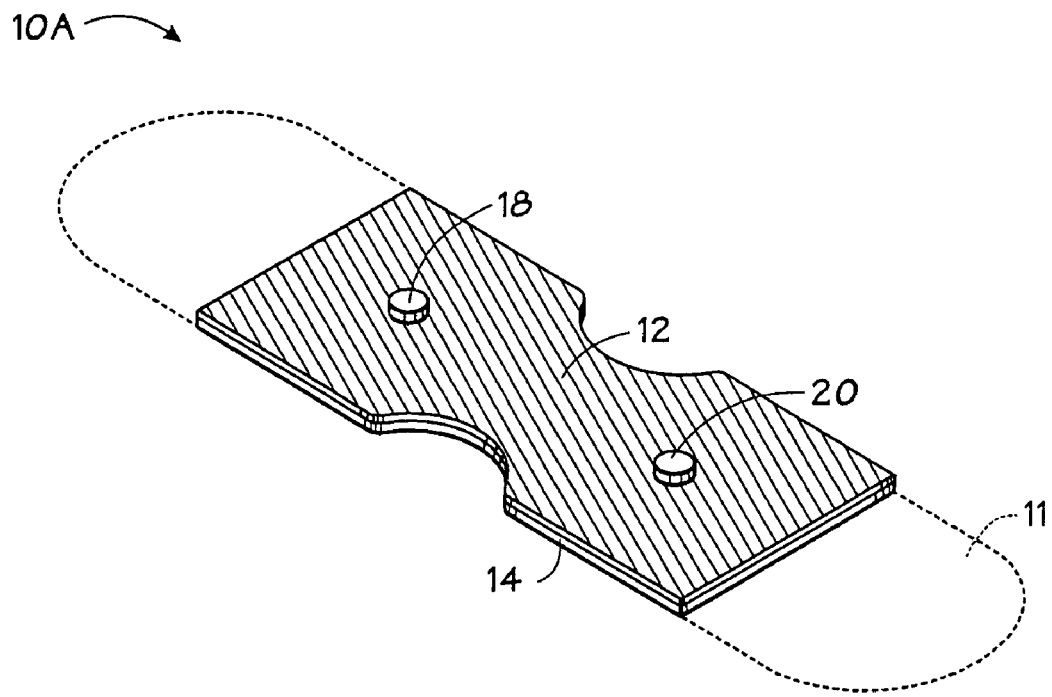
FIG. 1 illustrates a perspective view of an embodiment of an exemplary bandage-style sensor with an opaque, electrically nonconductive region in accordance with the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to eliminate or reduce the possible influence of light sources which may cause errors in pulse oximetry measurements. In accordance with the present techniques, pulse oximetry sensors are provided that reduce the amount of outside light that impinges the detecting elements of a sensor. Such sensors also reduce the amount of "shunted" light, i.e., light originating from light emitting elements of the sensor that impinges the detecting elements of a sensor without first passing through tissue. Sensors according to the present techniques incorporate features, such as a region of opaque material, on or near the tissue-contacting surface of the sensor, to prevent the undesired light from reaching the detecting elements of the sensor. Such regions may absorb, refract, or diffract the light from these undesired light sources before such light can impinge the detecting elements of the sensor.

The present sensors minimize the detection of unwanted external or shunted light to the sensor by application of an opaque, electrically nonconductive material to the body of the sensor. A substantially electrically nonconductive material may reduce electrical paths, interference and crosstalk between electrical signals. An opaque material is one that is substantially impenetrable by light and is not translucent. The opaque characteristics prevent external light from penetrating the region covered by opaque material while also absorbing shunted light.

Pulse oximetry sensors are typically placed on a patient in a location that is normally perfused with arterial blood to facilitate measurement of the desired blood characteristics, such as arterial oxygen saturation measurement ($SpO_2$). The most common sensor sites include a patient's fingertips, toes, earlobes or forehead. Regardless of the placement of a sensor used for pulse oximetry, the reliability of the measurement depends upon accurate detection of transmitted light that has passed through the perfused tissue which has not been supplemented by undesired light sources, such as external light or shunted light. Such supplementation or modulation of the light detected by the sensor can cause errors in the resulting pulse oximetry measurements.

In many cases, light from undesired light sources propagates along an optical path that is distinguishable from the optical path of the emitted light or signal light that is related to a blood constituent. Two common pulse oximetry sensors are the transmission-type sensor and the reflectance-type sensor. In a transmission-type sensor, the sensor's emitter and detector are positioned on opposing sides of the tissue when the sensor is applied to a patient. The optical path of the signal light, which is light originating from the emitter that properly passes through perfused tissue, is substantially in-line with an imaginary axis connecting the emitter and the detector. For reflectance-type sensors, the sensor's emitter and detector generally lie on the same side of the patient's tissue when applied. In reflectance-type sensors, the optical path of the emitted signal light is somewhat more complicated, as the light first enters the perfused tissue and then is scattered back to the detector. In both transmission-type and reflectance-type sensors, shunted light and ambient light generally propagate at angles substantially off-axis from the optical path of the signal light.

The exemplary sensors provided herein include opaque nonconductive regions that act to prevent shunted or external light from impinging on the light detecting elements of a sensor. In certain embodiments, those regions may be disposed on the sensor as layers, patterns, designs or a combination thereof. Specifically, FIG. 1 illustrates a perspective view of an embodiment of an exemplary bandage-style sensor 10A with an opaque, electrically nonconductive region 12 disposed on the sensor body 14. As one with skill in the art understands, the opaque, electrically nonconductive region 12 may be actually touching a patient's tissue, or may be almost touching the patient's tissue, depending on the closeness of the sensor's fit. As depicted, the region 12 is disposed on the entire tissue contacting surface of the sensor body 14, surrounding the emitter 20 and the detector 18. The sensor 10A may be applied to a patient's tissue with adhesive bandages 11. In certain embodiments, the opaque, electrically nonconductive region 12 may also include an adhesive layer configured to couple the region 12 to the patient.

Generally, it is envisioned that the opaque, electrically nonconductive region 12 will cover at least 75% of the tissue contacting surface of sensor body 14. In other embodiments, the opaque, electrically nonconductive region 12 may cover at least 25-65% of the surface area of the sensor body 14. The opaque, electrically nonconductive region 12 may be of variable size and configuration in relation to its placement on the sensor body 14 so as to optimize shielding from unwanted shunted and ambient light. In one embodiment, where the opaque, electrically nonconductive region 12 covers a portion of the tissue contacting surface, it is placed between emitter 20 and detector 18.

Figure 2:
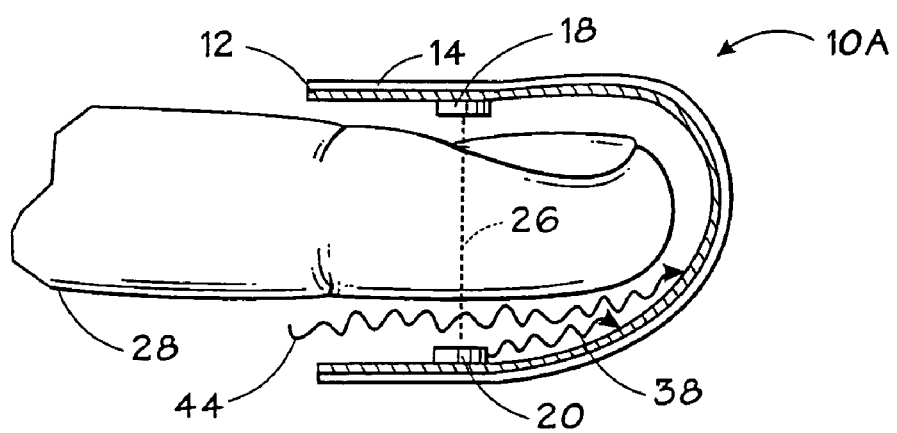
FIG. 2 illustrates a cross-sectional view of an embodiment of an exemplary bandage-style sensor with an opaque, electrically nonconductive region applied to the patient's digit.

Turning to FIG. 2, a cross-sectional view of the sensor 10A is depicted, in which a sensor body 14 including substantially opaque, electrically nonconductive region 12 is applied to a patient's digit 28. As depicted, the region 12 is disposed on a tissue-contacting surface of the sensor body 14. The optical path of signal light originating from the emitter 20 and through a patient's tissue is substantially in-line with an imaginary axis 26 connecting the emitter 20 and the detector 18. The detector 18 detects light and transmits the light measurement in the form of an electrical signal. A small percentage of the light emitted by the emitter 20 may not enter the perfused digit 28. Instead, this light may be shunted around the space between the digit 28 and the sensor body 14. The shunted light, depicted by wavy arrow 38, impinges the opaque, electrically nonconductive region 12, which absorbs the light, thus preventing it from reflecting around the gap between the sensor body 14 and the digit 28 and impinging on the detector 18. External light, depicted by wavy arrow 44, is similarly absorbed by the opaque, electrically nonconductive region 12. It should be understood that the gap between the sensor body 14 and the digit 28 may be very small for a sensor body 14 that conforms closely to the digit 28. Further, the gap may be discontinuous when interrupted by points where the sensor body 14 is touching the digit 28. The opaque region 12 reduces the overall reflectivity of the sensor body 14 on the tissue-contacting surface, which may reduce the amount of shunted light that reaches the detector 18. In addition, the substantially electrically nonconductive characteristic of region 12 reduces electrical interference and crosstalk between signals from the emitter 20 and detector 18, which may result in a reduction of measurement errors.

In certain embodiments, the opaque, electrically nonconductive region 12 as provided herein may include a material that may absorb at least about 90% to at least 95% of one or more wavelengths of visible light and near-infrared light. An opaque material may also absorb at least 50% of one or more wavelengths of light from the emitter, or may absorb a range of 50% to 95% of one or more wavelengths of light from the emitter. Examples of materials that may be used for the opaque, electrically nonconductive region 12 include nonconductive polymers, pigments, epoxy, fabrics (e.g. polyester-based materials) and silicone-based materials. The region 12 may be black or substantially dark in color. However, a thick light-colored region may also be sufficiently opaque. An opaque, electrically nonconductive region 12 may be applied to the sensor body 14 by painting, printing, or impregnating a film on the sensor body 14, or by adhesively applying the region 12 as a layer to the sensor body 14. The opaque, electrically nonconductive region 12 can be of variable thickness and may be one or more layers, depending upon the materials or application technique selected. The opaque, electrically nonconductive region 12 may be generally flexible, so as to allow the sensor 10 to conform to the patient's tissue. In certain embodiments, the opaque, electrically nonconductive region 12 is approximately 0.5 to 2.5 mils thick.

Figure 3:
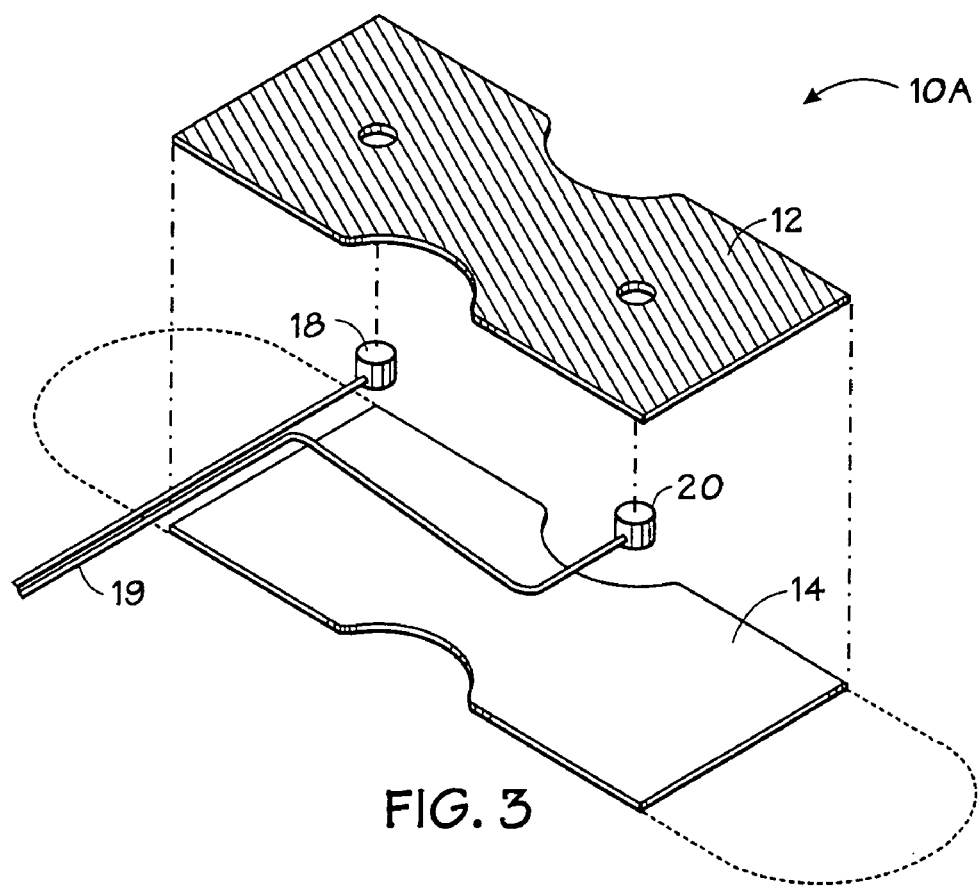
FIG. 3 illustrates an exploded view of the sensor of FIG. 1.

For example, FIG. 3 illustrates an exploded view of an embodiment of the bandage-style sensor 10A with an opaque, electrically nonconductive region 12 disposed on the sensor body 14. In certain embodiments, the emitter 20 and the detector 18 may be placed between the sensor body 14 and the opaque, electrically nonconductive region 12, protruding through holes in the opaque, electrically nonconductive region 12. The emitter 20 and detector 18 have leads 19 which connect the sensor 10A to the pulse oximetry system. As depicted, leads 19 are positioned near the center of sensor body 14, connecting the emitter 20 and detector 18 to a monitoring device. The opaque, electrically nonconductive region 12 is disposed to shield the leads 19, the emitter 20 and the detector 18, reducing crosstalk between signals.

Figure 4:
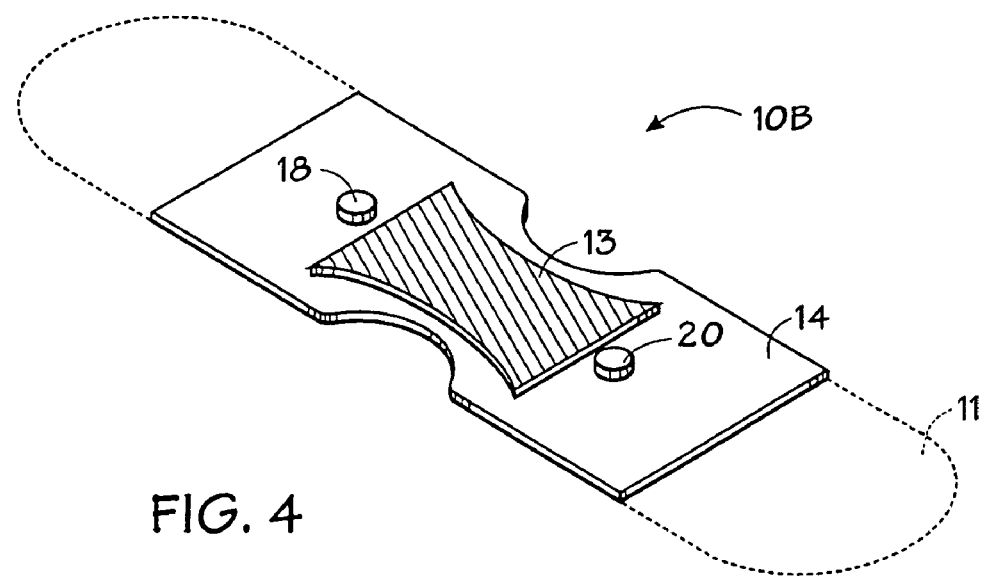
FIG. 4 illustrates a perspective view of an embodiment of an exemplary bandage-style sensor with an opaque, electrically nonconductive region disposed between the emitter and detector, in accordance with the present invention.
Figure 5:
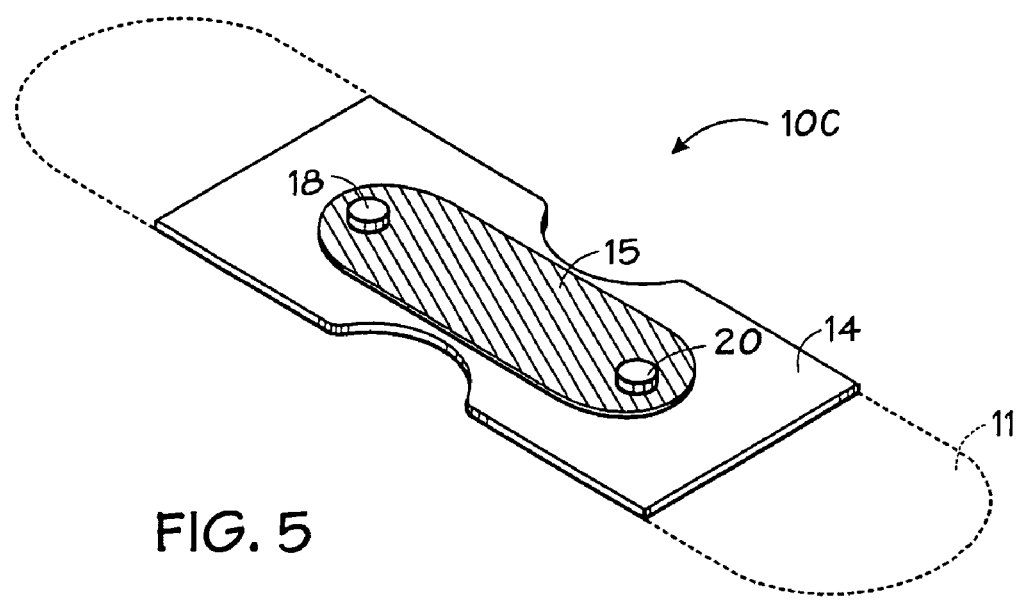
FIG. 5 illustrates a perspective view of an embodiment of an exemplary bandage-style sensor with an opaque, electrically nonconductive region in accordance with the present invention.

In certain embodiments, it may be advantageous to place opaque regions of differing patterns or designs on the sensor body. For example, FIG. 4 and FIG. 5 illustrate perspective views of bandage-style sensors with opaque nonconductive regions disposed on the sensor body. FIG. 4 illustrates a sensor 10B where the opaque, electrically nonconductive region 13 is disposed on the sensor body 14 between the emitter 20 and the detector 18. In an alternative embodiment, FIG. 5 illustrates a sensor 10C where the opaque, electrically nonconductive region 15, disposed on the sensor body 14, surrounds the emitter 20 and the detector 18. FIGS. 4 and 5 both depict adhesive bandages 11 for affixing the sensor to the patient's digit.

Figure 6:
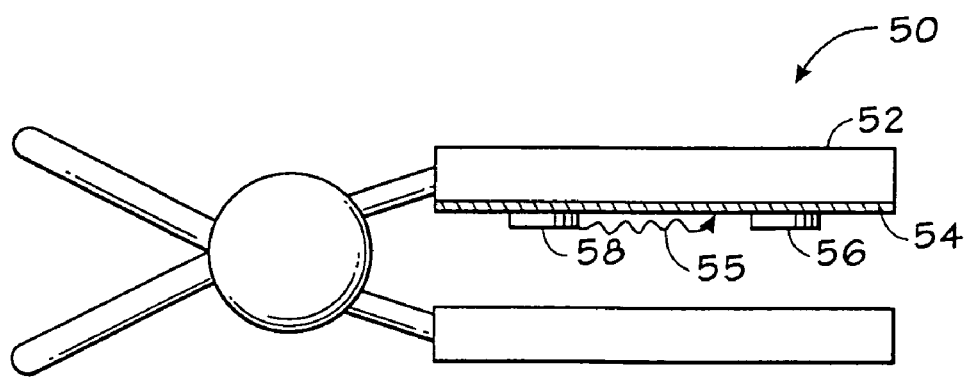
FIG. 6 illustrates a side view of an embodiment of an exemplary clip-style reflectance sensor with an opaque, electrically nonconductive region in accordance with the present invention.

FIG. 6 illustrates a side view of an embodiment of an exemplary clip-style reflectance sensor 50 with the opaque, electrically nonconductive region 54 disposed on the sensor body 52. In certain embodiments, the opaque, electrically nonconductive region 54 may be disposed on the entire tissue-contacting surface of the portion of the sensor body 52 where an emitter 58 and a detector 56 are disposed. As the emitted light, depicted by wavy arrow 55, strikes the opaque region 54, it is absorbed, preventing the unwanted light from impinging the detector 56. As stated above, it is desirable to avoid detection of the emitted light 55 as it has not traveled through the patient's tissue. The opaque, electrically nonconductive region 54 is disposed to shield the wire leads (not shown) to the emitter 58 and detector 56, reducing crosstalk between signals that may be transmitted to a downstream monitoring device, discussed below.

Figure 7:
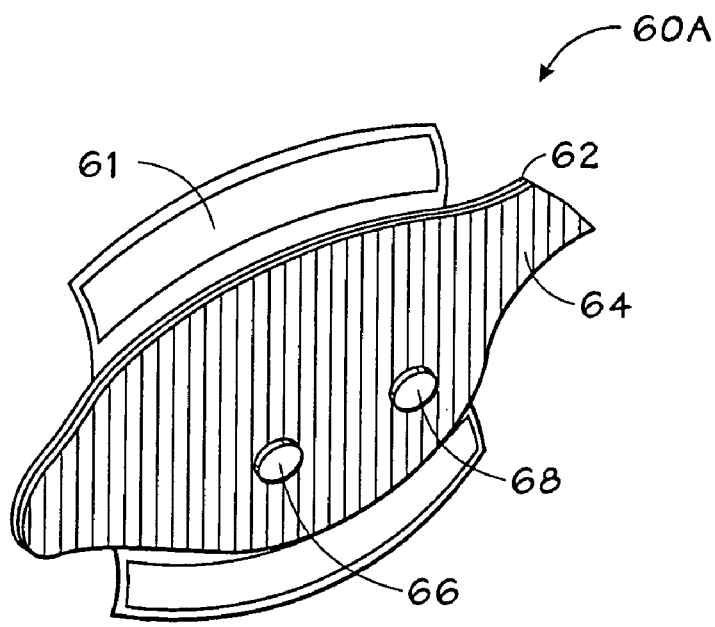
FIG. 7 illustrates a perspective view of an embodiment of an exemplary bandage-style reflectance sensor with an opaque, electrically nonconductive region in accordance with the present invention.
Figure 8:
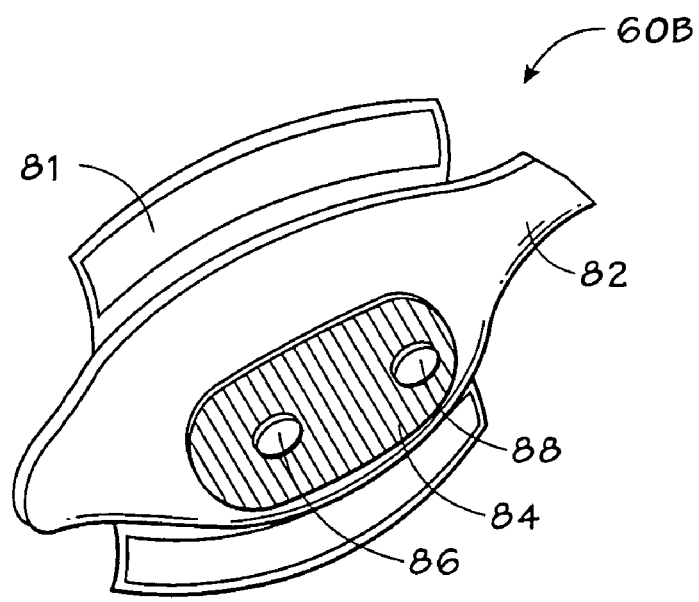
FIG. 8 illustrates a perspective view of an embodiment of an exemplary bandage-style reflectance sensor with an opaque, electrically nonconductive region in accordance with the present invention.

In another embodiment, FIG. 7 illustrates a perspective view of an exemplary bandage-style forehead sensor 60A with an opaque, electrically nonconductive region 64 disposed on a sensor body 62. The opaque, electrically nonconductive region 64 may be disposed on the entire tissue-contacting surface of the sensor body 62, surrounding emitter 68 and the detector 66. Alternatively, FIG. 8 illustrates an embodiment of an exemplary bandage-style reflectance sensor 60B with an opaque, electrically nonconductive region 84 disposed on a portion of the sensor body 82. As shown, the opaque, electrically nonconductive region 84 surrounds an emitter 88 and a detector 86. FIGS. 7 and 8 depict adhesive bandages 61 and 81, respectively, for affixing the sensor to the patient's tissue.

Figure 9:
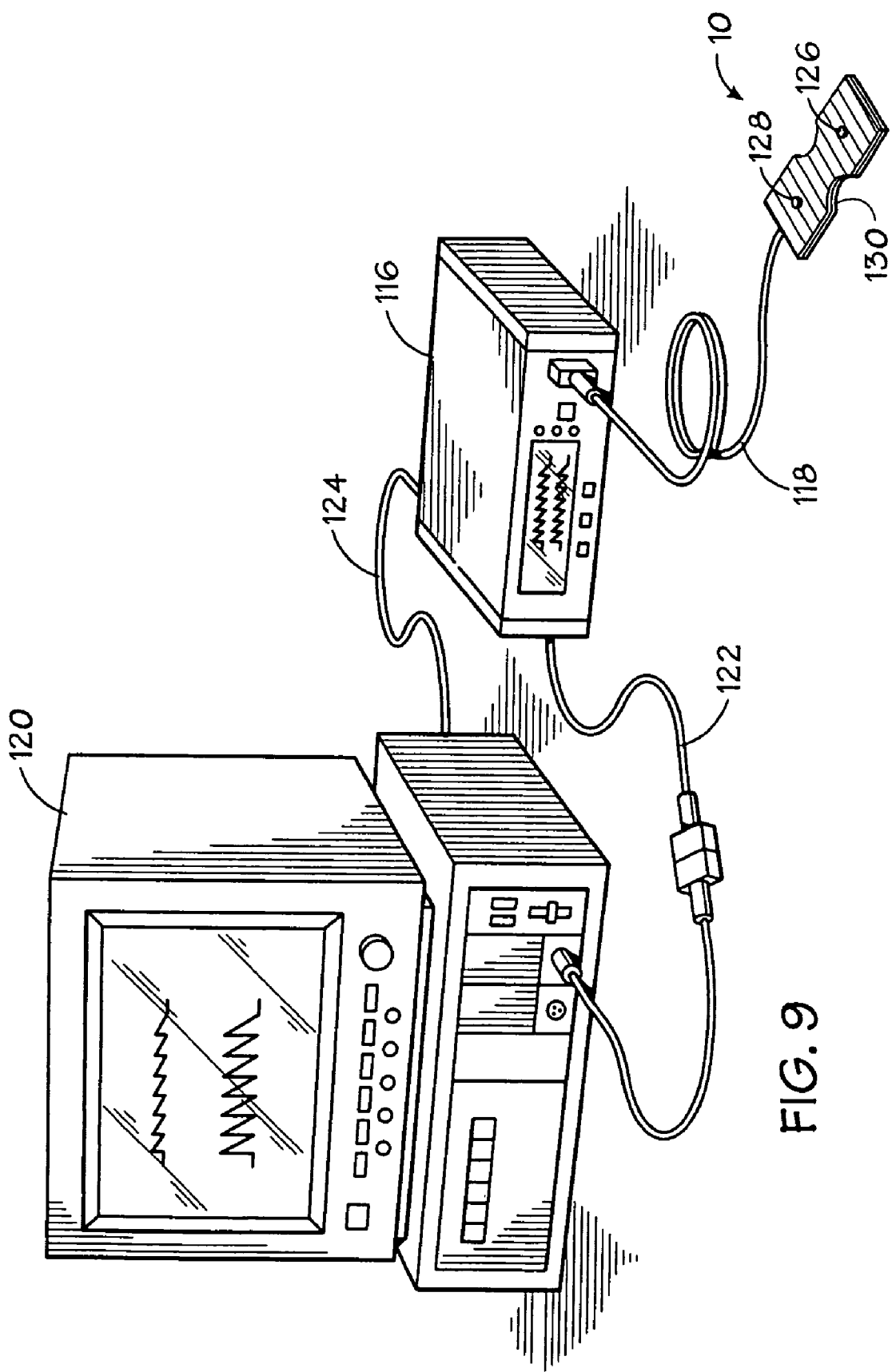
FIG. 9 illustrates a pulse oximetry system coupled to a multi-parameter patient monitor and a sensor according to embodiments of the present invention.

A sensor as provided herein, illustrated generically as a sensor 10, may be used in conjunction with a pulse oximetry monitor 116, as illustrated in FIG. 9. It should be appreciated that the cable 118 of the sensor 10 may be coupled to the monitor 116 or it may be coupled to a transmission device (not shown) to facilitate wireless transmission between the sensor 10 and the monitor 116. The monitor 116 may be any suitable pulse oximeter, such as those available from Nellcor Inc. Furthermore, to upgrade conventional pulse oximetry provided by the monitor 116 to provide additional functions, the monitor 116 may be coupled to a multi-parameter patient monitor 120 via a cable 122 connected to the sensor input port or via a cable 124 connected to a digital communication port.

The sensor 10 includes an emitter 128 and a detector 126 that may be of any suitable type. For example, the emitter 128 may be one or more light emitting diodes adapted to transmit one or more wavelengths of light in the red to infrared range, and the detector 126 may be a photodetector selected to receive light in the range or ranges emitted from the emitter 128. For pulse oximetry applications using either transmission or reflectance type sensors, the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The emitter 128 and the detector 126 may be disposed on a sensor body 130, which may be made of any suitable material, such as plastic, rubber, silicone, foam, woven material, or paper. Alternatively, the emitter 128 and the detector 126 may be remotely located and optically coupled to the sensor 10 using optical fibers. In the depicted embodiments, the sensor 10 is coupled to a cable 118 that is responsible for transmitting electrical and/or optical signals to and from the emitter 128 and detector 126 of the sensor 10. The cable 118 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 128 and detector 126 that are typically placed on opposing sides of the sensor site. If the sensor site is a fingertip, for example, the sensor 10 is positioned over the patient's fingertip such that the emitter 128 and detector 126 lie on either side of the patient's nail bed. In other words, the sensor 10 is positioned so that the emitter 128 is located on the patient's fingernail and the detector 126 is located 180° opposite the emitter 128 on the patient's finger pad. During operation, the emitter 128 shines one or more wavelengths of light through the patient's fingertip and the light received by the detector 126 is processed to determine various physiological characteristics of the patient. In each of the embodiments discussed herein, it should be understood that the locations of the emitter 128 and the detector 126 may be exchanged. For example, the detector 126 may be located at the top of the finger and the emitter 128 may be located underneath the finger. In either arrangement, the sensor 10 will perform in substantially the same manner.

Reflectance type sensors generally operate under the same general principles as transmittance type sensors. However, reflectance type sensors include an emitter 128 and detector 126 that are typically placed on the same side of the sensor site. For example, a reflectance type sensor may be placed on a patient's fingertip or forehead such that the emitter 128 and detector 126 lay side-by-side. Reflectance type sensors detect light photons that are scattered back to the detector 126.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
    a sensor body supporting respective electrical connectors connected to an emitter and a detector, wherein the emitter and the detector are disposed on a tissue-contacting surface of the sensor body; and
    at least one opaque member disposed on the sensor body and spanning only a portion of the sensor body between the emitter and the detector, the opaque member comprising a substantially electrically nonconductive material, and wherein the opaque member does not surround the emitter and detector.

2. The sensor, as set forth in claim 1, wherein the sensor comprises at least one of a pulse oximetry sensor or a sensor for measuring a water fraction.

3. The sensor, as set forth in claim 1, wherein the at least one opaque member comprises a polyester-based material.

4. The sensor, as set forth in claim 1, wherein the at least one opaque member comprises a silicone-based material.

5. The sensor, as set forth in claim 1, wherein the at least one opaque member is conformable to the tissue.

6. The sensor, as set forth in claim 1, wherein the emitter comprises at least one light emitting diode and the detector comprises at least one photodetector.

7. The sensor, as set forth in claim 1, wherein the at least one opaque member is substantially dark in color.

8. The sensor, as set forth in claim 1, wherein the at least one opaque member is substantially light in color.

9. A pulse oximetry system comprising:
    a pulse oximetry monitor; and
    a pulse oximetry sensor adapted to be operatively coupled to the monitor, the sensor comprising:
    a sensor body; and
    at least one opaque member disposed on the sensor body and covering at least a portion of the sensor body supporting respective electrical leads coupled to an emitter and a detector, the opaque member comprising a substantially electrically nonconductive material, and wherein the opaque member does not surround the emitter and detector.

10. The system, as set forth in claim 9, wherein the pulse oximetry sensor transmits an electrical signal, wherein the electrical signal comprises at least one measurement.

11. The system, as set forth in claim 9, wherein the at least one opaque member is disposed on at least 90% the sensor body.

12. The system, as set forth in claim 9, wherein the at least one opaque member is adhesively disposed on the sensor body.

13. The system, as set forth in claim 9, wherein the at least one opaque member comprises a polyester-based material.

14. The system, as set forth in claim 9, wherein the at least one opaque member comprises a silicone-based material.

15. The system, as set forth in claim 9, wherein the at least one opaque member comprises an adhesive material adapted to contact the tissue.

16. The system, as set forth in claim 9, wherein the at least one opaque member is conformable to patient tissue.

17. The system, as set forth in claim 9, wherein the emitter comprises at least one light emitting diode and the detector comprises at least one photodetector.

18. The system, as set forth in claim 9, wherein the pulse oximetry system comprises a multi-parameter monitor.

19. A method comprising:
emitting light into tissue with an emitter;
detecting the emitted light with a detector;
absorbing light that has not been transmitted from the emitter through the tissue with at least one opaque member disposed on a sensor body and covering at least a portion of the sensor body supporting respective electrical leads coupled to the emitter and the detector, wherein the at least one opaque member comprises a substantially electrically nonconductive material and wherein the opaque member does not surround the emitter and detector; and
measuring a physiological characteristic based on the detected light.

20. The method, as set forth in claim 19, wherein the at least one opaque member is adhesively disposed on the sensor body.

21. The method, as set forth in claim 20, wherein the at least one opaque member is disposed on a tissue-contacting surface of the sensor body.

22. The method, as set forth in claim 19, wherein the sensor comprises at least one of a pulse oximetry sensor or a sensor for measuring a water fraction.

23. The method, as set forth in claim 19, wherein the at least one opaque member comprises a polyester-based material.

24. The method, as set forth in claim 19, wherein the at least one opaque member comprises a silicone-based material.

25. A method of manufacturing a sensor, comprising:
providing a sensor body supporting respective electrical connectors coupled to an emitter and a detector, wherein the emitter and the detector are disposed on the sensor body; and
providing at least one opaque member disposed on the sensor body and spanning only a portion of the sensor body in a region between the emitter and the detector, the opaque member comprising a substantially electrically nonconductive material, and wherein the opaque member does not surround the emitter and detector.

26. The method, as set forth in claim 25, wherein providing the emitter comprises providing one or more light emitting diodes and providing the detector comprises providing one or more photodetectors.

27. The method, as set forth in claim 25, wherein the sensor comprises at least one of a pulse oximetry sensor or a sensor for measuring a water fraction.

28. The method, as set forth in claim 25, wherein providing the at least one opaque member comprises adhesively disposing the opaque region on the sensor body.

29. The method, as set forth in claim 25, wherein providing the at least one opaque member comprises providing a polyester-based material.

30. The method, as set forth in claim 25, wherein providing the at least one opaque member comprises providing a silicone-based material.

31. The method, as set forth in claim 25, comprising providing an adhesive material on the opaque member adapted to contact the tissue.

* * * * *